(12) United States Patent
Fujita et al.

(10) Patent No.: US 9,513,252 B2
(45) Date of Patent: Dec. 6, 2016

(54) GAS SENSOR

(71) Applicant: NGK SPARK PLUG CO., LTD., Nagoya-shi, Aichi (JP)

(72) Inventors: Tomohisa Fujita, Iwakura (JP); Nobuhiro Inoue, Tajimi (JP); Makoto Kume, Inuyama (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 236 days.

(21) Appl. No.: 14/511,334

(22) Filed: Oct. 10, 2014

(65) Prior Publication Data

US 2015/0101394 A1     Apr. 16, 2015

(30) Foreign Application Priority Data

Oct. 16, 2013  (JP) ................ 2013-215210
Aug. 4, 2014   (JP) ................ 2014-158415

(51) Int. Cl.
*G01N 27/407*        (2006.01)

(52) U.S. Cl.
CPC .................. *G01N 27/4077* (2013.01)

(58) Field of Classification Search
CPC ................................. G01N 27/4077
USPC ............................. 73/23.31, 21.32
See application file for complete search history.

(56) References Cited

U.S. PATENT DOCUMENTS

| | | | | |
|---|---|---|---|---|
| 5,238,552 A * | 8/1993 | Kato | .......... | G01N 27/4077 204/428 |
| 6,279,376 B1 * | 8/2001 | Yamada | .......... | G01N 27/4077 73/23.2 |
| 6,346,179 B1 * | 2/2002 | Makino | .......... | G01N 27/4077 204/426 |
| 6,691,553 B2 * | 2/2004 | Holleboom | .......... | G01N 27/4077 73/23.32 |
| 7,007,543 B2 * | 3/2006 | Sakawa | .......... | G01N 27/4077 204/424 |
| 7,607,340 B2 * | 10/2009 | Nakashima | .......... | G01N 27/4077 204/426 |
| 7,708,869 B2 * | 5/2010 | Yamada | .......... | G01N 27/4071 204/428 |
| 7,901,556 B2 * | 3/2011 | Yamada | .......... | G01N 27/4077 204/424 |
| 8,351,658 B2 | 1/2013 | Adachi et al. | | |
| 8,449,743 B2 * | 5/2013 | Sekiya | .......... | G01N 27/4077 204/424 |
| 8,464,573 B2 | 6/2013 | Sekiya et al. | | |
| 8,857,241 B2 * | 10/2014 | Nakashima | .......... | G01N 27/4077 204/424 |
| 2008/0016948 A1 * | 1/2008 | Yamada | .......... | G01N 27/4077 73/31.05 |
| 2011/0126610 A1 | 6/2011 | Sekiya et al. | | |
| 2011/0209523 A1 * | 9/2011 | Otsubo | .......... | G01N 27/4077 73/23.31 |

FOREIGN PATENT DOCUMENTS

JP       2011-112557 A       6/2011

* cited by examiner

*Primary Examiner* — John Fitzgerald
(74) *Attorney, Agent, or Firm* — Sughrue Mion, PLLC

(57) ABSTRACT

In a gas sensor (100), a base end portion (175b) of a second outer wall (175) of an outer protector (171) is connected airtightly to a forward end portion (164c) of a first inner wall (164) of an inner protector (161), and relations of A≤B<C<D and (0.6×B)≤A are satisfied, wherein A represents the total opening area of a second outer hole (176) of the outer protector (171), B represents the total opening area of a second inner hole (166) of the inner protector (161), C represents the total opening area of a first inner hole (167), and D represents the total opening area of a first outer hole.

10 Claims, 6 Drawing Sheets

GAS SENSOR

BACKGROUND OF THE INVENTION

1. Field of the Invention

The present invention relates to a gas sensor including a detection element which is exposed to a gas-to-be-detected in order to detect a particular gas component contained in the gas, and more particularly, to a gas sensor having a protector for protecting the detection element from adhesion of water or the like.

2. Description of the Related Art

A gas sensor has conventionally been known which is attached to an exhaust pipe for use in an automobile or the like. The gas sensor includes a detection element which generates an electromotive force having a magnitude which changes in accordance with the concentration of a particular gas, such as NOx (nitrogen oxides) or oxygen, contained in the exhaust gas, or a detection element whose resistance changes in accordance with the concentration of the particular gas. In such a gas sensor, if a water droplet contained in the exhaust gas adheres to the detection element when heated to a high temperature, the detection element may suffer damage, such as cracking, due to thermal shock. Therefore, a protector covering the detection element is attached to the gas sensor so as to protect the detection element from the adhesion of water (see, for example, Patent Document 1).

[Patent Document 1] Japanese Patent Application Laid-Open (kokai) No. 2011-112557

The gas sensor of Patent Document 1 includes a sensor element (detection element); a first protection cover (inner protector) which covers the sensor element and which has a first gas introduction hole permitting a gas-to-be measured (gas-to-be-detected) to flow from the outside of the first protection cover to the inside thereof; a second protection cover (outer protector) which covers the first protection cover and which has a second gas introduction hole permitting the gas-to-be measured to flow from the outside of the second protection cover to the inside thereof; and a gas flow passage which extends from the second gas introduction hole to the first gas introduction hole through a space between the first protection cover and the second protection cover, extends from the first gas introduction hole into the interior of the first protection cover, and reaches a forward end of the sensor element.

Further, in the gas sensor of Patent Document 1, at least one of the first protection cover and the second protection cover has an inner wall member which is solid or has a closed space therein and which is disposed to reduce the width of at least a portion of a flow passage which is a portion of the gas flow passage and which inner wall member extends from the second gas introduction hole to the first gas introduction hole.

3. Problems to be Solved by the Invention

Also, in the gas sensor of Patent Document 1, a through-hole (inner gas discharge hole) is formed in the side wall of a forward end portion of the inner protector so as to discharge the gas-to-be-detected from the inside of the inner protector to the outside thereof. Moreover, a through-hole (outer gas discharge hole) is formed in a bottom portion of a forward end portion of the outer protector which surrounds the forward end portion of the inner protector in order to discharge the gas-to-be-detected from the inside of the outer protector to the outside thereof. Notably, the outer gas discharge hole is formed on the center axis of the outer protector. Also, the forward end portion of the outer protector has a cylindrical side wall and a disk-like bottom portion.

In the gas sensor of Patent Document 1 configured as described above, the gas-to-be-detected taken into the interior of the gas sensor is discharged to the outside thereof through the following route. Specifically, the gas-to-be-detected introduced into the internal space of the inner protector is discharged from the internal space to a side (radially outer side) through the inner gas discharge hole, and flows through the space between the side wall of the forward end portion of the outer protector and the side wall of the forward end portion of the inner protector. Subsequently, the gas-to-be-detected flows through the space toward the axially forward end side, and then flows through the gap between the bottom portion of the outer protector and the bottom portion of the inner protector toward the center axis. The gas-to-be-detected is then discharged to the outside of the protector through the outer gas discharge hole formed in the bottom portion of the outer protector.

However, when the above-mentioned gas discharge passage is employed, difficulty is encountered in introducing a gas-to-be-detected into the internal space of the inner protector efficiently and quickly and in discharging the thus-introduced gas-to-be-detected to the outside efficiently and quickly, whereby the responsiveness of the gas sensor may deteriorate.

Particularly, in recent years, strict regulations have been imposed on exhaust gas emission from internal combustion engines, and accordingly, a demand has arisen for a gas sensor capable of monitoring a difference in exhaust gas pressure between cylinders. Although such an inter-cylinder difference may be monitored by employing gas sensors provided on the respective cylinders, employing a plurality of gas sensors leads to an increase in cost. Therefore, in a known method, a single gas sensor is provided on an exhaust gas assembly of a multi-cylinder engine for monitoring the air/fuel ratio in the respective cylinders. The gas sensor employed in such a method must quickly respond to the exhaust gas originating from each cylinder.

SUMMARY OF THE INVENTION

The present invention was made in view of the above circumstances, and an object thereof is to provide a gas sensor having a protector which is improved in gas introduction performance and gas discharge performance to thereby enhance the responsiveness of the gas sensor and which can properly protect a detection element from adhesion of water.

The above object has been achieved, in accordance with a first aspect (1) of the invention, by providing a gas sensor comprising a detection element extending in an axial direction and having a detection portion which is provided on a forward end side thereof and adapted to detect a particular gas component contained in a gas-to-be-detected; a housing which surrounds a circumference of the detection element such that the detection portion projects from a forward end of the housing; and a protector which is fixed to the housing and which surrounds the circumference of the detection portion, the protector including an inner protector which accommodates the detection portion in an internal space of the inner protector, and an outer protector which accommodates the inner protector, wherein the inner protector includes a tubular first inner wall having a first inner hole extending therethrough, a tubular second inner wall which is located on an axially forward end side of the first inner wall and which has a diameter smaller than that of the first inner wall, the second inner wall having a second inner hole extending therethrough, and an inner bottom wall which closes a forward end of the second inner wall; the outer protector includes a tubular first outer wall which surrounds the circumference of the first inner wall to define a tubular first space between the first outer wall and the first inner wall, the first outer wall having a first outer hole extending therethrough at a position on the axially forward end side in relation to the first inner hole, a tubular second outer wall which is located on the axially forward end side of the first outer wall, which has a diameter smaller than that of the first outer wall and larger than that of the first inner wall, and which surrounds the circumference of the second inner wall to define a tubular second space between the second outer wall and the second inner wall, the second outer wall having a base end portion which radially overlaps a forward end portion of the first inner wall, and extending toward the axially forward end side in relation to the inner bottom wall, and an outer bottom wall located on the axially forward end side of the second outer wall and having a second outer hole; and relations of $A \leq B < C < D$ and $(0.6 \times B) \leq A$ are satisfied, wherein A represents the total opening area of the second outer hole, B represents the total opening area of the second inner hole, C represents the total opening area of the first inner hole, and D represents the total opening area of the first outer hole.

In the gas sensor (1) above, the gas-to-be-detected flows through the interior of the protector along the following route. Specifically, the gas-to-be-detected is introduced into the first space (the space between the first outer wall and the first inner wall) from the outside through the first outer hole of the outer protector (outer gas introduction hole). The gas-to-be-detected then flows within the first space toward the axially base end side, and is introduced into the internal space of the inner protector through the first inner hole of the inner protector (inner gas introduction hole). Thereafter, the gas-to-be-detected flows within the internal space toward the axially forward end side, is discharged to the outside of the inner protector through the second inner hole of the inner protector (inner gas discharge hole), and is introduced into the second space (the space between the second outer wall and the second inner wall). After being introduced into a space between the outer bottom wall of the outer protector and the inner bottom wall of the inner protector, the gas-to-be-detected is discharged to the outside of the protector through the second outer hole of the outer protector (outer gas discharge hole).

Notably, the first inner hole of the inner protector is located on the axially base end side in relation to the detection portion of the detection element, and the second inner hole is located on the axially forward end side in relation to the detection portion of the detection element. Therefore, a portion of the gas-to-be-detected introduced into the internal space through the first inner hole is led to the detection portion of the detection element in the course of flowing within the internal space toward the axially forward end side and is discharged to the outside of the inner protector through the second inner hole.

In the case where the base end portion of the second outer wall of the outer protector does not radially overlap with the forward end portion of the first inner wall of the inner protector, a portion of the gas-to-be-detected introduced into the first space from the outside through the first outer hole flows into the second space through the gap between the second outer wall and the first inner wall, and then flows (or flows under resistance) into the internal space of the inner protector through the second inner hole. Therefore, the gas introduced into the internal space of the inner protector through the first inner hole is prevented from being discharged to the outside of the inner protector through the second inner hole. As a result, the gas discharge performance may deteriorate.

In contrast, in the gas sensor (1), the base end portion (portion opposite the forward end portion) of the second outer wall of the outer protector radially overlaps the forward end portion of the first inner wall of the inner protector over the entire circumference thereof around the axis.

Therefore, the gas-to-be-detected introduced into the first space from the outside through the first outer hole does not easily flow from the first space directly to the second space, and flows within the first space toward the axially base end side, and can be introduced through the first inner hole into the internal space (space which accommodates the detection portion of the detection element) of the inner protector. Thus, the gas-to-be-detected introduced into the internal space of the inner protector through the first inner hole can be smoothly discharged to the outside of the inner protector through the second inner hole.

In the gas sensor (1), as described above, the gas-to-be-detected introduced into the internal space of the inner protector through the first inner hole of the inner protector flows within the internal space toward the axially forward end side, and is discharged to the outside of the inner protector through the second inner hole of the inner protector. The gas-to-be-detected is then discharged to the outside of the protector through the second outer hole of the outer protector. Incidentally, the smaller the opening area of a hole, the more difficult it is for the gas to pass through the hole. Accordingly, of the second outer hole, the second inner hole, and the first inner hole, a hole which has the smallest opening area (total opening area) determines the amount (discharge rate) of the gas discharged to the outside of the protector (discharge performance).

In contrast, in the gas sensor (1), the total opening area A of the second outer hole, the total opening area B of the second inner hole, the total opening area C of the first inner hole, and the total opening area D of the first outer hole satisfy the relation $A \leq B < C < D$. Thus, of the total opening areas of the second outer hole, the second inner hole, the first inner hole, and the first outer hole, the total opening area A of the second outer hole is made smallest (or equal to the total opening area B of the second inner hole). Therefore, in the above-described gas sensor, the amount of gas discharged to the outside of the protector (discharge performance) is adjusted by the second outer hole without being affected by the gas discharge performances of the second inner hole, the first outer hole, and the first inner hole.

Also, in the gas sensor (1), of the total opening areas of the first outer hole, the first inner hole, the second inner hole, and the second outer hole, the total opening area D of the first outer hole is made largest. Therefore, the gas is easily introduced from the outside into the protector through the first outer hole. Thus, the responsiveness of the gas sensor can be enhanced. Since the total opening area C of the first inner hole is made largest next to the total opening area D of the first outer hole, exhaust gas is easily introduced into the internal space of the inner protector through the first inner hole, whereby the responsiveness of the gas sensor can be enhanced.

In the gas sensor (1), a relation of $(0.6 \times B) \leq A$ is also satisfied. Thus, since the total opening area A of the second outer hole is adjusted to be equal to or larger than (0.6×the total opening area B of the second inner hole), the gas discharge performance of the second outer hole is enhanced, and the flow rate of the gas-to-be-detected, which flows within the protector and reaches the detection element, is increased. Therefore, the responsiveness of the gas sensor can be further enhanced.

In the case where a plurality of second outer holes are provided, the "total opening area" of the second outer hole is the sum of the opening areas of the second outer holes. This also applies to the first outer hole, the second inner hole, and the first inner hole. The number of the second outer holes, the number of the first inner holes, the number of the first outer holes, and the number of the second inner holes, or the opening area per hole of the second outer holes, that of the first inner holes, that of the first outer holes, and that of the second inner holes may be appropriately set so as to satisfy the above-described relation among their total opening areas.

Also, the gas sensor (1) has an inner bottom wall which closes the forward end of the second inner wall. That is, the inner bottom wall of the inner protector does not have a through-hole which penetrates the inner bottom wall. Thus, the second outer hole of the outer bottom wall and the inner bottom wall of the inner protector overlap each other as viewed in the axial direction. Therefore, even when water enters from the outside to the interior of the protector through the second outer hole of the outer bottom wall, the inner bottom wall of the inner protector prevents the water from flowing directly into the interior of the inner protector. Thus, the detection element accommodated within the inner protector can be properly protected from adhesion of water.

Furthermore, in the gas sensor (1), the first outer hole is provided on the forward end portion of the first outer wall, and the first inner hole is provided on the base end portion of the first inner wall. That is, the first outer hole and the first inner hole are provided so as not to overlap each other in the axial direction. Therefore, the first inner hole can be largely separated from the first outer hole toward the axially base end side. Thus, even when water enters through the first outer hole, the water hardly reaches the first inner hole and hardly flows into the interior of the inner protector through the first inner hole. Accordingly, the detection element can be further protected from adhesion of water.

In a second aspect (2), the present invention provides a gas sensor comprising a detection element extending in an axial direction and having a detection portion which is provided on a forward end side thereof and adapted to detect a particular gas component contained in a gas-to-be-detected; a housing which surrounds a circumference of the detection element such that the detection portion projects from a forward end of the housing; and a protector which is fixed to the housing and which surrounds the circumference of the detection portion, the protector including an inner protector which accommodates the detection portion in an internal space of the inner protector, and an outer protector which accommodates the inner protector, wherein the inner protector includes a tubular first inner wall having a first inner hole extending therethrough, a tubular second inner wall which is located on an axially forward end side of the first inner wall and which has a diameter smaller than that of the first inner wall, the second inner wall having a second inner hole extending therethrough, and an inner bottom wall which closes a forward end of the second inner wall; the outer protector includes a tubular first outer wall which surrounds the circumference of the first inner wall to define a tubular first space between the first outer wall and the first inner wall, the first outer wall having a first outer hole extending therethrough at a position on the axially forward end side in relation to the first inner hole, a tubular second outer wall which is located on the axially forward end side of the first outer wall, which has a diameter smaller than that of the first outer wall and larger than that of the first inner wall, and which surrounds the circumference of the second inner wall to define a tubular second space between the second outer wall and the second inner wall, the second outer wall having a base end portion which radially overlaps a forward end portion of the first inner wall, and extending toward the axially forward end side in relation to the inner bottom wall, and an outer bottom wall located on the axially forward end side of the second outer wall and having a second outer hole; a relation of $A \leq B < C < D$ is satisfied, wherein A represents the total opening area of the second outer hole, B represents the total opening area of the second inner hole, C represents the total opening area of the first inner hole, and D represents the total opening area of the first outer hole; and D3 is smaller than D1 and smaller than D2, wherein D1 represents the axially shortest distance between the second outer hole and the second inner hole, D2 represents the axially shortest distance between the second inner hole and the first inner hole, and D3 represents the axially shortest distance between the first inner hole and the first outer hole.

In the gas sensor (2), the gas-to-be-detected flows through the interior of the protector along the same route as in the case of the first mode. In the gas sensor, the first inner hole of the inner protector is located on the axially base end side in relation to the detection portion of the detection element, and the second inner hole is located on the axially forward end side in relation to the detection portion of the detection element. Therefore, a portion of the gas-to-be-detected introduced into the internal space through the first inner hole is led to the detection portion of the detection element in the course of flowing within the internal space toward the axially forward end side and discharged to the outside of the inner protector through the second inner hole.

In the gas sensor (2), the base end portion (portion opposite the forward end portion) of the second outer wall of the outer protector radially overlaps with the forward end portion of the first inner wall of the inner protector over the entire circumference around the axis. Therefore, the gas-to-be-detected introduced into the first space from the outside through the first outer hole does not easily flow from the first space directly to the second space. Rather, the gas-to-be-detected flows within the first space toward the axially base end side, and can be introduced through the first inner hole into the internal space (space which accommodates the detection portion of the detection element) of the inner protector. Thus, the gas-to-be-detected introduced into the internal space of the inner protector through the first inner hole can be smoothly discharged to the outside of the inner protector through the second inner hole.

In the gas sensor (2), the total opening area A of the second outer hole, the total opening area B of the second inner hole, the total opening area C of the first inner hole, and the total opening area D of the first outer hole satisfy the relation $A \leq B < C < D$. Thus, of the total opening areas of the second outer hole, the second inner hole, the first inner hole, and the first outer hole, the total opening area A of the second outer hole is made smallest (or equal to the total opening area B of the second inner hole). Therefore, in the above-described gas sensor, the amount of gas discharged to the outside of the protector (discharge performance) is adjusted by the second outer hole without being affected by the gas discharge performances of the second inner hole, the first outer hole, and the first inner hole.

Also, in the gas sensor (2), of the total opening areas of the first outer hole, the first inner hole, the second inner hole, and the second outer hole, the total opening area D of the first outer hole is made largest. Therefore, the gas is easily introduced from the outside into the protector through the first outer hole. Thus, the responsiveness of the gas sensor can be enhanced. Since the total opening area C of the first inner hole is made largest next to the total opening area D of the first outer hole, exhaust gas is easily introduced into the internal space of the inner protector through the first inner hole, whereby the responsiveness of the gas sensor can be enhanced.

Furthermore, in the gas sensor (2), the axially shortest distance D3 between the first inner hole and the first outer hole is smaller than D1 and smaller than D2. When the distance D3 is made shortest, the gas-to-be-detected is easily introduced from the outside into the protector, since the gas introduced into the protector first passes between the first outer hole and the first inner hole. Thus, the responsiveness of the gas sensor can be enhanced.

As used herein, the term "axially shortest distance" between holes refers to the shortest linear distance between the holes in the axial direction. For example, the shortest distance D3 between the first inner hole and the first outer hole corresponds to the axially shortest linear distance between the base-end-side peripheral edge of the first outer hole and the forward-end-side peripheral edge of the first inner hole as viewed in a radial direction perpendicular to the axial direction. When a plurality of first outer holes are provided in the axial direction as described below, the shortest distance D3 corresponds to the axially shortest distance between the forward-end-side peripheral edge of the first inner hole and the base-end-side peripheral edge of the first outer hole (among the plurality of first outer holes) which is located nearest to the base end.

Also, the gas sensor (2) has an inner bottom wall which closes the forward end of the second inner wall. That is, the inner bottom wall of the inner protector does not have a through-hole which penetrates the inner bottom wall. Thus, the second outer hole of the outer bottom wall and the inner bottom wall of the inner protector overlap each other as viewed in the axial direction. Therefore, even when water enters from the outside to the interior of the protector through the second outer hole of the outer bottom wall, the inner bottom wall of the inner protector prevents the water from flowing directly into the interior of the inner protector. Thus, the detection element accommodated within the inner protector can be properly protected from adhesion of water.

In addition, in the gas sensor (2), the first outer hole is provided on the forward end portion of the first outer wall, and the first inner hole is provided on the base end portion of the first inner wall. That is, the first outer hole and the first inner hole are provided so as not to overlap each other in the axial direction. Therefore, the first inner hole can be separated to a large extent from the first outer hole toward the axially base end side. Thus, even when water enters through the first outer hole, the water hardly reaches the first inner hole and hardly flows into the interior of the inner protector through the first inner hole. Accordingly, the detection element can be further protected from adhesion of water.

In a preferred embodiment (3) of any of the gas sensors (1) and (2) above, preferably, the base end portion of the second outer wall is connected airtightly to the forward end portion of the first inner wall.

In the case where the base end portion of the second outer wall of the outer protector is not connected to the forward end portion of the first inner wall of the inner protector in an airtight manner (in a state in which gas cannot flow through the connected portion), it is difficult to completely prevent the circumstance where a portion of the gas-to-be-detected introduced into the first space from the outside through the first outer hole flows into the second space through the gap between the second outer wall and the first inner wall, and then flows (or flows under resistance) into the internal space of the inner protector through the second inner hole. In such a circumstance, the gas introduced into the internal space of the inner protector through the first inner hole is prevented from being discharged to the outside of the inner protector through the second inner hole. Thus, the gas discharge performance may deteriorate.

In contrast, in the gas sensor (3), the base end portion of the second outer wall of the outer protector is connected to the forward end portion of the first inner wall of the inner protector over the entire circumference around the axis in an airtight manner (in a state in which gas cannot flow through the connected portion).

Therefore, the gas-to-be-detected introduced into the first space from the outside through the first outer hole does not flow from the first space directly to the second space, and flows within the first space toward the axially base end side without fail, and is introduced through the first inner hole into the internal space of the inner protector (space which accommodates the detection portion of the detection element). As a result, the gas-to-be-detected introduced into the internal space of the inner protector through the first inner hole can be smoothly discharged to the outside of the inner protector through the second inner hole.

Notably, the base end portion of the second outer wall and the forward end portion of the first inner wall may be connected together by crimping, fitting, or welding.

In another preferred embodiment (4) of any of the gas sensors (1) to (3) above, a plurality of first outer holes are provided in the axial direction.

When, as described above, the shortest distance D3 is made smallest; i.e., the first outer hole approaches the first inner hole in the axial direction, the responsiveness of the gas sensor can be enhanced. However, when the first outer hole approaches the first inner hole, the first outer hole and the first inner hole axially overlap each other. In that case, when water enters from the outside into the first outer hole, the water easily flows directly into the first inner hole (into the inner protector). In contrast, when a plurality of first outer holes are provided in the axial direction, water entering through the first outer holes is easily discharged to the outside, and is prevented from flowing into the inner protector, whereby the detection element accommodated within the inner protector can be properly protected from adhesion of water.

In yet another preferred embodiment (5) of any of the gas sensors (1) to (4) above, the outer bottom wall is tapered toward the axially forward end side.

As shown in FIG. 4, exhaust gas G flows along the outer bottom wall from the upstream side (left side) of an exhaust pipe to the downstream side (right side) thereof. When the outer bottom wall is tapered, by virtue of the Venturi effect, a strong negative pressure is produced in the vicinity of the second outer hole on the forward end side of the outer bottom wall, whereby the gas-to-be-detected within the protector is easily discharged through the second outer hole. Therefore, the above-described gas sensor exhibits further improved gas discharge performance.

In yet another preferred embodiment (6) of any of the gas sensors (1) to (5) above, the detection element has a gas introduction portion for introducing the gas-to-be-detected into the detection portion, and the first inner hole is located on the axially base end side in relation to the gas introduction portion.

In the gas sensor (6), a portion of the gas-to-be-detected introduced into the internal space through the first inner hole flows within the internal space toward the axially forward end side, and then is discharged to the outside of the inner protector through the second inner hole. Since the gas introduction portion of the detection element is provided in the course of this gas flow, the gas-to-be-detected can be reliably introduced into the detection portion.

DESCRIPTION OF REFERENCE NUMERALS

Figure 1:
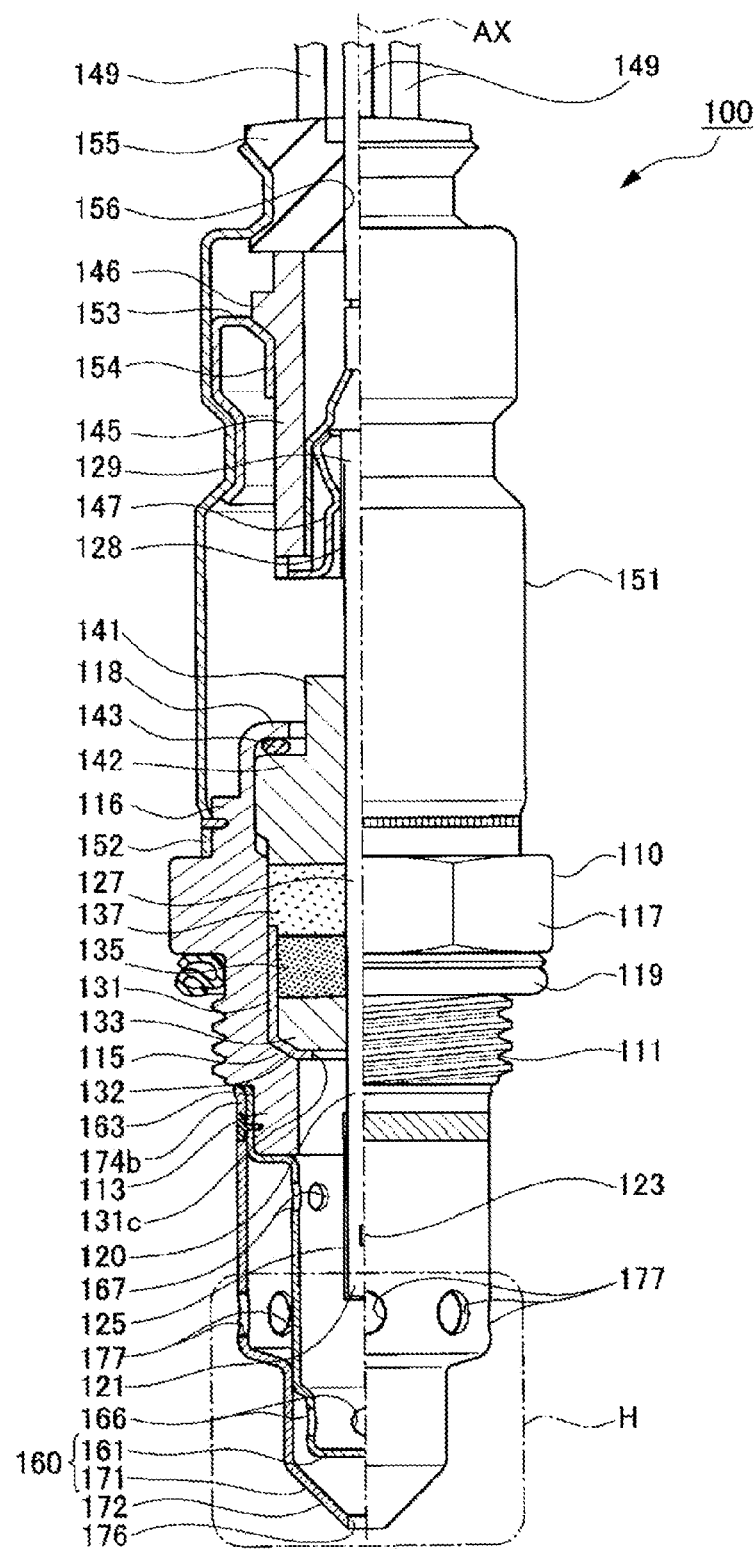
FIG. 1 is a half sectional view of a gas sensor of an embodiment according to a first mode of the present invention.

Reference numerals used to identify various features in the drawings including the following.
100, 200: gas sensor
110: metallic shell (housing)
113: forward end fixing portion of metallic shell (forward end portion of housing)
120: detection element
121: detection portion
123: gas introduction portion
160: protector
161: inner protector
162: inner bottom wall
164: first inner wall
164c: forward end portion of first inner wall
165: second inner wall
166: second inner hole
167: first inner hole
171, 271: outer protector
172, 272: taper wall (outer bottom wall)
174, 274: first outer wall
175, 275: second outer wall
175b, 275b: base end portion of second outer wall
176, 276: second outer hole
177, 277, 2771, 2772: first outer hole
AX: axis
G: exhaust gas (gas-to-be-detected)
D1: diameter of first inner hole (diameter of inscribed circle of first inner hole)
D2: diameter of first outer hole (diameter of inscribed circle of first outer hole)
S1: first space
S2: second space
S3: internal space
S4: in-taper space

DETAILED DESCRIPTION OF THE PREFERRED EMBODIMENTS

Embodiments

Embodiments of the invention will next be described in greater detail with reference to the drawings. However, the present invention should not be construed as being limited thereto.

Figure 2:
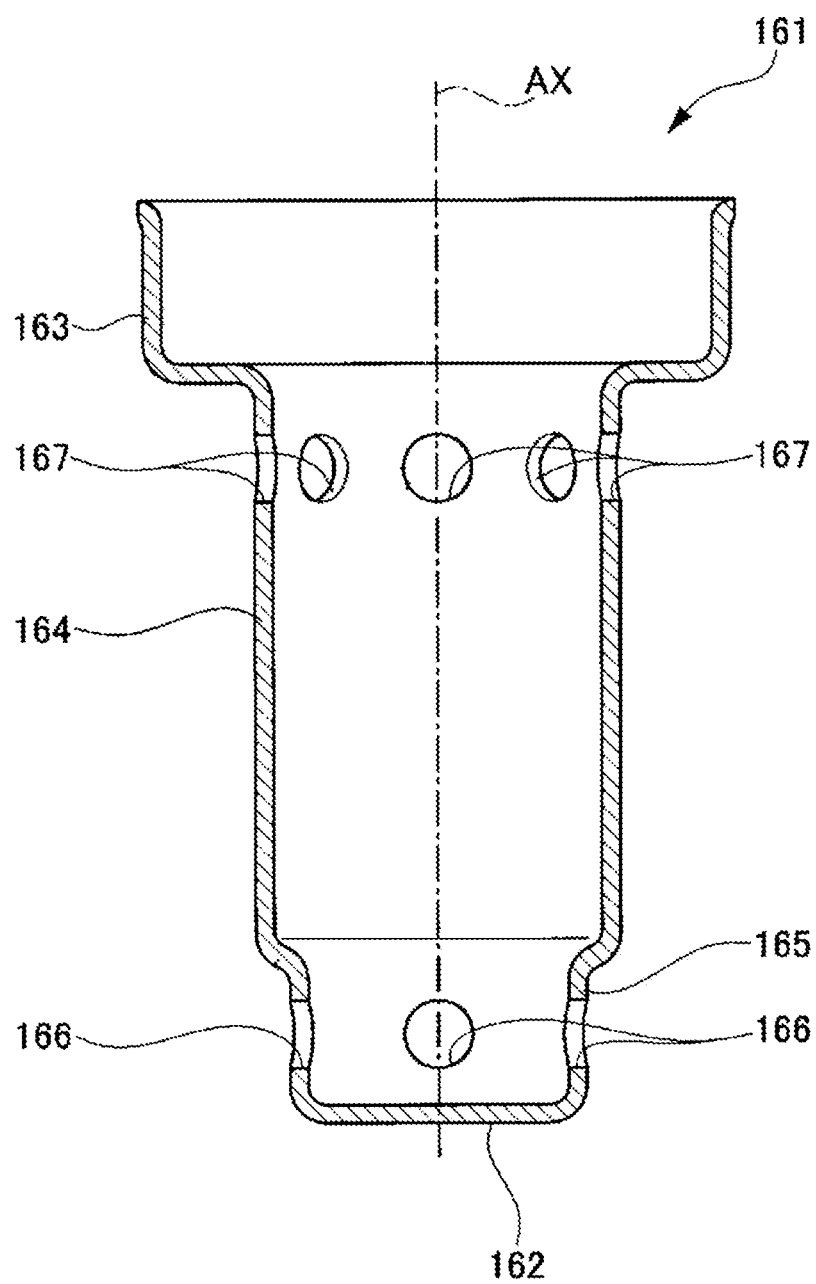
FIG. 2 is a sectional view of an inner protector of the gas sensor.
Figure 3:
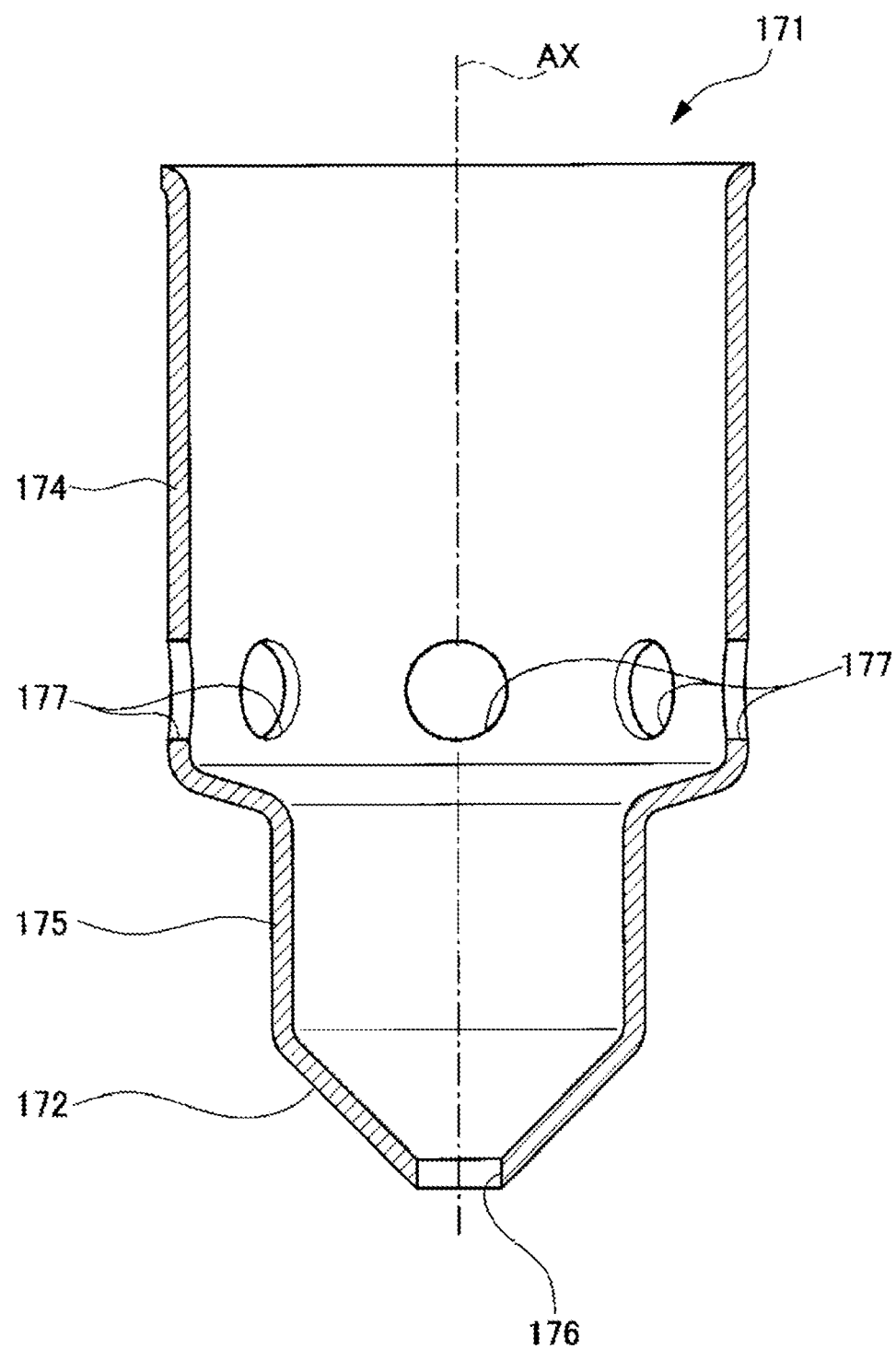
FIG. 3 is a sectional view of an outer protector of the gas sensor.
Figure 4:
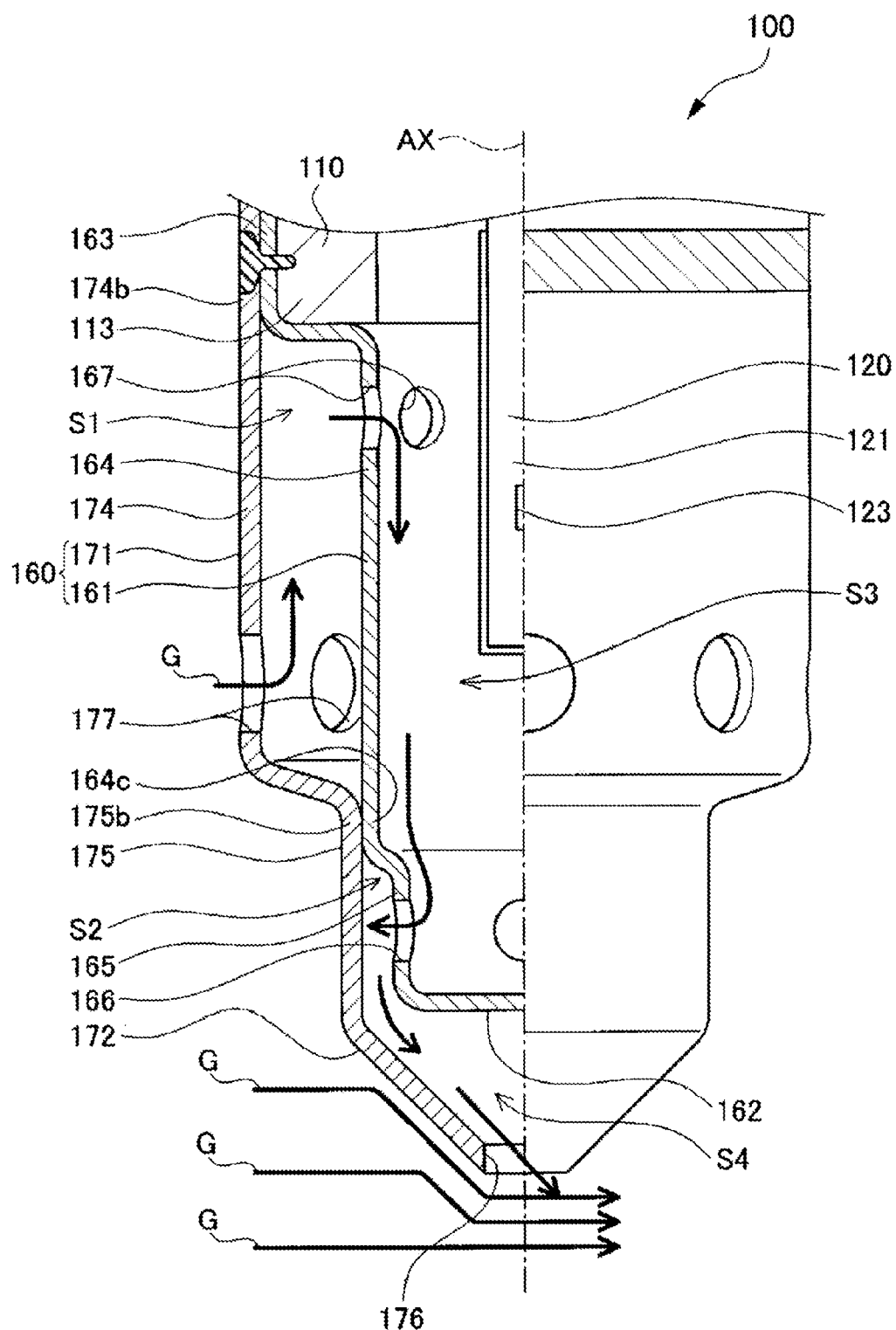
FIG. 4 is a view used for describing the flow of a gas-to-be-detected within the gas sensor.

FIG. 1 is a half sectional view of a gas sensor 100 of an embodiment according to the first mode of the present invention. FIG. 2 is a sectional view of an inner protector 161 of the gas sensor 100. FIG. 3 is a sectional view of an outer protector 171 of the gas sensor 100. FIG. 4 is an enlarged view of a forward end portion of the gas sensor 100 which is attached to an exhaust pipe of an unillustrated automobile such that the forward end portion of the gas sensor 100 is located within the exhaust pipe. FIG. 4 is used for describing the flow of exhaust gas (gas-to-be-detected) G.

Notably, in FIGS. 1 to 4, the lower side is an axially forward end side (hereinafter also referred to as the forward end side), and the upper side is an axially base end side (hereinafter also referred to as the base end side). Also, in FIG. 4, the left side is the upstream side (engine side) of the exhaust pipe through which exhaust gas G flows, and the right side is the downstream side of the exhaust pipe.

The gas sensor 100 is a so-called full range air/fuel ratio sensor which is attached to the exhaust pipe of an unillustrated automobile and which holds therein a detection element 120. A detection portion 121 of the detection element 120 is exposed to exhaust gas (gas-to-be-detected) which flows through the exhaust pipe so as to detect the air/fuel ratio of the exhaust gas from the concentration of oxygen (particular gas component) contained in the exhaust gas.

As shown in FIG. 1, the gas sensor 100 is mainly composed of a tubular metallic shell (housing) 110 extending in an axial direction (the direction along an axis AX, the vertical direction in FIG. 1); the plate-shaped detection element 120 held inside the metallic shell 110; a sheath 151 fixedly provided on the base end side of the metallic shell 110; and a double-wall protector 160 which is fixedly provided on the forward end side of the metallic shell 110 and which is composed of an inner protector 161 and an outer protector 171.

The detection element 120 has a plate-like shape (strip-like shape) extending in the axial direction, and a forward end portion of the detection element 120 is the detection portion 121 for detecting the oxygen gas component contained in the exhaust gas. This detection element 120 has a known structure and is formed by bonding together for unification a plate-shaped gas detecting body for detecting oxygen concentration and a plate-shaped heater body for heating the gas detecting body for quick activation thereof. The gas detecting body is composed of a solid electrolyte body which predominantly contains zirconia, and a pair of electrodes (detection and reference electrodes) which predominantly contains platinum. The pair of electrodes are disposed on the detection portion 121.

The detection portion 121 has a gas introduction portion 123 for introducing the exhaust gas into the interior of the element. This gas introduction portion 123 is formed of a porous material and has a rectangular shape in a planar view. In order to protect the detection electrode from poisoning by the exhaust gas, a protection layer 125 is provided on the detection portion 121 such that the protection layer 125 covers the outer surface of the detection portion 121. Also, five electrode pads 128 (one of which is shown in FIG. 1) for allowing external connection with the electrodes of the gas detecting body and the heater body are formed on a base end portion 129 of the detection element 120.

A closed-bottomed tubular metal cup 131 is disposed at a position slightly deviated forward from the center of a trunk portion 127 of the detection element 120 such that the detection element 120 is inserted through the interior of the metal cup 131 with the detection portion 121 projecting from an opening 131c formed in the bottom of the metal cup 131. The metal cup 131 is a member for holding the detection element 120 in the metallic shell 110. A forward-end peripheral edge portion 132 of the metal cup 131 is tapered such that the diameter of the metal cup 131 decreases toward the forward end thereof.

The metal cup 131 contains a ceramic ring 133 made of alumina and a first talc ring 135 formed by compacting a talc powder, in such a manner that the detection element 120 is inserted through the ceramic ring 131 and through the first talc ring 135. The first talc ring 135 is compressed within the metal cup 131 so as to tightly fill an associated space, thereby holding the detection element 120 in position in the metal cup 131.

The detection element 120 united with the metal cup 131 is held by the tubular metallic shell 110 such that its circumference is surrounded by the metallic shell 110. The metallic shell 110 is adapted to fixedly attach the gas sensor 100 to the exhaust pipe of an automobile. The metallic shell 110 is formed from low-carbon steel such as SUS430. An external thread portion 111 for attachment to the exhaust pipe is formed on the forward end side of the outer circumference of the metallic shell 110. The metallic shell 110 has an annular forward end fixing portion 113 which is projectingly formed on the forward end side of the external thread portion 111 and to which the protector 160 described below is fixed.

The metallic shell 110 also has a tool engagement portion 117 which is formed at the center of the outer circumference of the metallic shell 110 and with which a mounting tool is engaged. In order to prevent leakage of gas when the gas sensor 100 is attached to the exhaust pipe, a gasket 119 is fitted to a portion of the metallic shell 110 between the tool engagement portion 117 and the external thread portion 111. The metallic shell 110 further has a base end fixing portion 116 which is formed on the base end side of the tool engagement portion 117 and to which the sheath 151 described below is fixed. The metallic shell 110 further has a crimp portion 118 which is formed on the base end side of the base end fixing portion 116 and which is adapted to crimp-hold the detection element 120 in the metallic shell 110.

The metallic shell 110 has a stepped portion 115 which is formed on the forward end side of the inner circumference of the metallic shell 110 and which is tapered such that its diameter decreases toward the forward end side. The tapered front-end peripheral edge portion 132 of the metal cup 131 which holds the detection element 120 is engaged with the stepped portion 115.

Furthermore, a second talc ring 137 is disposed in the metallic shell 110 to be located on the base end side of the metal cup 131 so that the detection element 120 is inserted through the second talc ring 137. A tubular sleeve 141 is fitted into the metallic shell 110 so as to press the second talc ring 137 from the base end side of the second talc ring 137.

The sleeve 141 has a step-like shoulder portion 142. An annular crimp packing 143 is disposed on the shoulder portion 142. The crimp portion 118 of the metallic shell 110 is crimped so as to press the shoulder portion 142 of the sleeve 141 toward the forward end side via the crimp packing 143.

Being pressed by the sleeve 141, the second talc ring 137 is crushed within the metallic shell 110, thereby tightly filling an associated space. By means of the second talc ring 137 and the first talc ring 135, which is previously placed in the metal cup 131, the metal cup 131 and the detection element 120 are held in position in the metallic shell 110. The crimp packing 143 disposed between the crimp portion 118 and the shoulder portion 142 of the sleeve 141 maintains the airtightness of the interior of the metallic shell 110, to thereby prevent leakage of combustion gas.

A base end portion 129 of the detection element 120 projects toward the base end side beyond the crimp portion 118, which is the base end portion of the metallic shell 110. The base end portion 129 is covered with a tubular separator 145 formed from an electrically insulative ceramic. The separator 145 internally holds five connection terminals 147 (one of which is shown in FIG. 1) electrically connected to the five electrode pads 128 formed on the base end portion 129 of the detection element 120. Also, the separator 145 accommodates connection portions between the connection terminals 147 and corresponding five lead wires 149 (three of which are shown in FIG. 1), which extend to the exterior of the gas sensor 100, while insulating them from one another.

The tubular sheath 151 is disposed so as to surround the circumference of the separator 145. The sheath 151 is made of stainless steel (SUS304 in the present embodiment). A forward end opening portion 152 of the sheath 151 is disposed on the radially outer side of the base end fixing portion 116 of the metallic shell 110. The forward end opening portion 152 is crimped radially inward, and laser welding is performed on the forward end opening portion 152 along the entire outer circumference thereof, whereby the forward end opening portion 152 is connected to the base end fixing portion 116.

A tubular metal holder 153 is disposed in the gap between the sheath 151 and the separator 145. The metal holder 153 has a support portion 154, which is formed by inwardly bending a base end of the metal holder 153. The separator 145 is inserted through the metal holder 153 such that a flange portion 146 formed on the outer circumference of a base end portion of the separator 145 is engaged with the support portion 154, whereby the separator 145 is supported by the support portion 154. In this condition, a portion of the sheath 151 where the metal holder 153 is disposed is crimped radially inward, whereby the metal holder 153 which supports the separator 145 is fixed to the sheath 151.

A grommet 155 made of fluorine-containing rubber is fitted into a base end opening of the sheath 151. The grommet 155 has five insertion holes 156 (one of which is shown in FIG. 1). The five lead wires 149 extending outwardly from the separator 145 are airtightly inserted through the respective insertion holes 156. In this condition, while the grommet 155 presses the separator 145 toward the forward end side, a portion of the sheath 151 which corresponds to the grommet 155 is crimped radially inward, whereby the grommet 155 is fixed to the sheath 151.

The detection portion 121 of the detection element 120 held by the metallic shell 110 projects from the forward end fixing portion 113, which is a forward end portion of the metallic shell 110. The protector 160 is fitted to the forward end fixing portion 113 so as to protect the detection portion 121 of the detection element 120 from fouling with deposits (poisoning substances, such as fuel ash and oil) contained in exhaust gas and from breakage caused by adhesion of water. The protector 160 is fixed to the forward end fixing portion 113 by laser welding. The protector 160 includes a tubular inner protector 161 having a bottom, and an outer protector 171 which accommodates the inner protector 161 (see FIGS. 1 to 4).

As shown in FIG. 4, the inner protector 161 is fixed to the metallic shell 110 in a state in which the detection portion 121 of the detection element 120 is disposed in the internal space S3 of the inner protector 161. As shown in FIGS. 1, 2, and 4, the inner protector 161 has a base end portion 163; a first inner wall 164 located on the axially forward end side (the lower side in FIGS. 1, 2, and 4) of the base end portion 163; a second inner wall 165 located on the axially forward end side of the first inner wall 164, and a disk-like inner bottom wall 162 which closes the forward end of the second inner wall 165.

The first inner wall 164 has a cylindrical tubular shape and has first inner holes 167 which penetrate the first inner wall 164. Notably, in the present embodiment, eight first inner holes 167 having the same shape (same dimension) are formed at equal intervals in the circumferential direction. All of the eight first inner holes 167 are located on the axially base end side (the upper side in FIGS. 1 and 4) in relation to the detection portion 121 of the detection element 120.

The second inner wall 165 has a cylindrical tubular shape, is smaller in diameter than the first inner wall 164, and has second inner holes 166 which penetrate the second inner wall 165. Notably, in the present embodiment, four second inner holes 166 are formed at equal intervals in the circumferential direction. All the four second inner holes 166 are located on the axially forward end side (the lower side in FIGS. 1 and 4) in relation to the detection portion 121 of the detection element 120.

Notably, although the inner diameters of the first inner wall 164 and the second inner wall 165 are smaller than the outer diameter of the forward end fixing portion 113 of the metallic shell 110, the base end portion 163 has an increased diameter such that the base end portion 163 is located on the outer side of the forward end fixing portion 113.

The outer protector 171 is fixed to the metallic shell 110 in a state in which the outer protector 171 accommodates the inner protector 161 therein. The outer protector 171 has a first outer wall 174; a second outer wall 175 located on the axially forward end side of the first outer wall 174, and a taper wall 172 (corresponding to the "outer bottom wall" of the invention) located on the axially forward end side of the second outer wall 175 (see FIGS. 1, 3, and 4).

The first outer wall 174 has a cylindrical tubular shape, and surrounds the circumference of the first inner wall 164 while forming a tubular first space S1 in cooperation with the first inner wall 164 of the inner protector 161. Further, the first outer wall 174 has first outer holes 177 which penetrate the first outer wall 174 and are located on the axially forward end side in relation to the first inner holes 167 of the inner protector 161 (see FIGS. 1 and 4). Notably, in the present embodiment, eight first outer holes 177 having the same shape (same dimension) are formed at equal intervals in the circumferential direction. All the eight first outer holes 177 are located on the axially forward end side in relation to the first inner holes 167 of the inner protector 161.

The second outer wall 175 has a cylindrical tubular shape, and has an inner diameter smaller than the inner diameter of the first outer wall 174 and larger than the outer diameter of the first inner wall 164. Further, the second outer wall 175 surrounds the circumference of the second inner wall 165 while forming a tubular second space S2 in cooperation with the second inner wall 165. The second outer wall 175 extends to a point on the axially forward end side of the inner bottom wall 162 of the inner protector 161.

In particular, in the present embodiment, the second outer wall 175 is connected at its base end portion 175b to a forward end portion 164c of the first inner wall 164 in an airtight manner (in a state in which gas cannot flows through the connected portion). Specifically, the base end portion 175b of the second outer wall 175 and the forward end portion 164c of the first inner wall 164 are airtightly connected (fitted) together over the entire circumference around the axis AX by press-fitting the forward end portion 164c of the first inner wall 164 into the base end portion 175b of the second outer wall 175.

The taper wall 172 has the shape of a tapered tube (truncated conical tube) whose diameter decreases toward the axially forward end side. This taper wall 172 has a second outer hole 176, which is a forward end opening of the outer protector 171. In particular, in the present embodiment, the entirety of the taper wall 172 is disposed on the axially forward end side in relation to the inner bottom wall 162 of the inner protector 161.

The base end portion 174b of the first outer wall 174 of the outer protector 171 is disposed on the outer side of the base end portion 163 of the inner protector 161. Laser welding is performed along the entire outer circumference of the base end portion 174b of the outer protector 171 so as to fix (weld) the base end portion 174b of the outer protector 171, together with the base end portion 163 of the inner protector 161, to the forward end fixing portion 113 of the metallic shell 110.

In the gas sensor 100 of the present embodiment, the exhaust gas (gas-to-be-detected) G within the exhaust pipe flows through the interior of the protector 160 (the inner protector 161 and the outer protector 171) along the following route.

Specifically, as shown in FIG. 4, the exhaust gas G having flowed through the exhaust pipe from the upstream side thereof (the left side in FIG. 4) toward the gas sensor 100 is introduced into the first space S1 within the protector 160 (the space between the first outer wall 174 and the first inner wall 164) through the first outer holes 177 of the outer protector 171 (outer gas introduction holes).

The exhaust gas G then flows within the first space S1 toward the axially base end side (the upper side in FIG. 4), and is introduced into the internal space S3 of the inner protector 161 through the first inner holes 167 of the inner protector 161 (inner gas introduction holes). After that, the exhaust gas G flows within the internal space S3 toward the axially forward end side (the lower side in FIG. 4), is discharged to the outside of the inner protector 161 through the second inner holes 166 of the inner protector 161 (inner gas discharge holes), and is introduced into the second space S2 (the space between the second outer wall 175 and the second inner wall 165). After being introduced into an in-taper space S4 surrounded by the taper wall 172 of the outer protector 171, the exhaust gas G is discharged to the outside of the protector 160 through the second outer hole 176 of the outer protector 171 (outer gas discharge hole).

Notably, the first inner holes 167 of the inner protector 161 are located on the axially base end side in relation to the detection portion 121 of the detection element 120, and the second inner holes 166 are located on the axially forward end side in relation to the detection portion 121. Therefore, a portion of the exhaust gas G introduced into the internal space S3 through the first inner holes 167 is led to the gas introduction portion 123 of the detection portion 121 in the course of flowing within the internal space S3 toward the axially forward end side and being discharged to the outside of the inner protector 161 through the second inner holes 166.

In the case where the base end portion of the second outer wall of the outer protector is not connected to the forward end portion of the first inner wall of the inner protector in an airtight manner (in a state in which gas cannot flow through the connected portion), a portion of the exhaust gas G introduced into the first space S1 from the outside through the first outer holes flows into the second space through the gap between the second outer wall and the first inner wall, and then flows (or flows under resistance) into the internal space of the inner protector through the second inner holes. Therefore, the gas introduced into the internal space of the inner protector through the first inner holes is prevented from being discharged to the outside of the inner protector through the second inner holes. As a result, the gas discharge performance may deteriorate.

In contrast, in the gas sensor 100 of the present embodiment, the base end portion 175*b* of the second outer wall 175 of the outer protector 171 radially overlaps with and is connected to (fitted onto) the forward end portion 164*c* of the first inner wall 164 of the inner protector 161 over the entire circumference thereof around the axis in an airtight manner (in a state in which gas cannot flow through the connected portion).

Therefore, the exhaust gas G introduced into the first space S1 from the outside through the first outer holes 177 does not flow from the first space S1 directly to the second space S2. Instead, the exhaust gas G flows within the first space S1 toward the axially base end side without fail, and is introduced into the internal space S3 of the inner protector 161 (space which accommodates the detection portion 120 of the detection element 120) through the first inner holes 167 (see FIG. 4). As a result, the exhaust gas G introduced into the internal space S3 of the inner protector 161 through the first inner holes 167 can be smoothly discharged to the outside of the inner protector 161 through the second inner holes 166.

Further, in the gas sensor 100 of the present embodiment, the exhaust gas G introduced into the interior of the outer protector 171 from the outside through the first outer holes 177 of the outer protector 171 flows through the first inner holes 167 of the inner protector 161 into the internal space S3, then flows within the internal space S3 toward the axially forward end side (the lower side in FIG. 4), and is discharged to the outside of the inner protector 161 through the second inner holes 166 of the inner protector 161. The exhaust gas G is then discharged to the outside of the protector 160 through the second outer hole 176 of the outer protector 171.

The smaller the opening area of a hole, the more difficult it is for the exhaust gas G to pass through the hole. Accordingly, of the second outer hole 176, the second inner holes 166, and the first inner holes 167, a hole(s) which has the smallest opening area (total opening area) determines the amount of the exhaust gas G discharged to the outside of the protector 160 (discharge performance).

In contrast, in the gas sensor 100 of the present embodiment, the total opening area A of the second outer hole 176, the total opening area B of the second inner holes 166, the total opening area C of the first inner holes 167, and the total opening area D of the first outer holes 177 satisfy a relation of $A \leq B < C < D$. That is, of the total opening areas of the second outer hole 176, the second inner holes 166, the first inner holes 167, and the first outer holes 177, the total opening area A of the second outer hole 176 is made smallest. Accordingly, in the gas sensor 100 of the embodiment, the amount of gas discharged to the outside of the protector 160 (discharge performance) is adjusted by the second outer hole 176 without being affected by the gas discharge performances of the second inner holes 166, the first outer holes 177, and the first inner holes 167.

In addition, of the total opening areas of the first outer holes 177, the first inner holes 167, the second inner holes 166, and the second outer hole 176, the total opening area D of the first outer holes 177 is made largest. Therefore, the exhaust gas G is easily introduced from the outside into the protector 160 through the first outer holes 177. Thus, the responsiveness of the gas sensor can be enhanced. Since the total opening area C of the first inner holes 167 is made largest next to the total opening area D of the first outer holes 177, the exhaust gas G is easily introduced into the internal space S3 of the inner protector 161 through the first inner holes 167, whereby the responsiveness of the gas sensor can be enhanced.

Notably, in the present embodiment, a plurality of (four) second inner holes 166 are provided; i.e., the "total opening area" of the second inner holes 166 is the sum of the opening areas of the second inner holes 166; a plurality of (eight) first inner holes 167 are provided; i.e., the "total opening area" of the first inner holes 167 is the sum of the opening areas of the first inner holes 167; and a plurality of (eight) first outer holes 177 are provided; i.e., the "total opening area" of the first outer holes 177 is the sum of the opening areas of the first outer holes 177.

Furthermore, in the gas sensor 100 of the present embodiment, a relation of $(0.6 \times B) \leq A$ is satisfied. Thus, since the total opening area A of the second outer hole is adjusted to be equal to or larger than (0.6×the total opening area B of the second inner holes), as described below, the gas discharge performance of the second outer hole is enhanced, and the flow rate of the gas-to-be-detected, which flows within the protector and reaches the detection element, is increased. Therefore, the responsiveness of the gas sensor can be further enhanced.

Notably, in the present embodiment, the forward end fixing portion 113 of the metallic shell 110 corresponds to the "forward end portion of the housing" of the invention.

Also, in the gas sensor 100 of the embodiment, the forward end of the inner protector 161 (the forward end of the second inner wall 165) is closed by the inner bottom wall 162. That is, the inner bottom wall 162 of the inner protector 161 does not have a through-hole which penetrates the inner bottom wall 162. As a result, the second outer hole 176 of the taper wall 172 and the inner bottom wall 162 of the inner protector 161 overlap each other as viewed in the axial direction. Therefore, even when external water enters the interior of the protector 160 through the second outer hole 176 of the taper wall 172, the inner bottom wall 162 of the inner protector 161 prevents the water from flowing directly into the interior of the inner protector 161. As a result, it is possible to properly protect the detection element 120 accommodated within the inner protector 161 from adhesion of water.

Further, in the gas sensor 100 of the embodiment, the first outer holes 177 are disposed at the forward end portion of the first outer wall 174, and the first inner holes 167 are disposed at the base end portion of the first inner wall 164.

As a result, the first inner holes 167 can be separated to a large extent from the first outer holes 177 toward the axially base end side. Therefore, even when water enters through the first outer holes 177, the water becomes less likely to reach the first inner holes 167, and becomes less likely to flow into the interior of the inner protector 161 through the first inner holes 167. Therefore, the water becomes more unlikely to adhere to the detection element 120.

Next, an embodiment according to the second mode of the present invention will be described with reference to FIG. 5.

Figure 5:
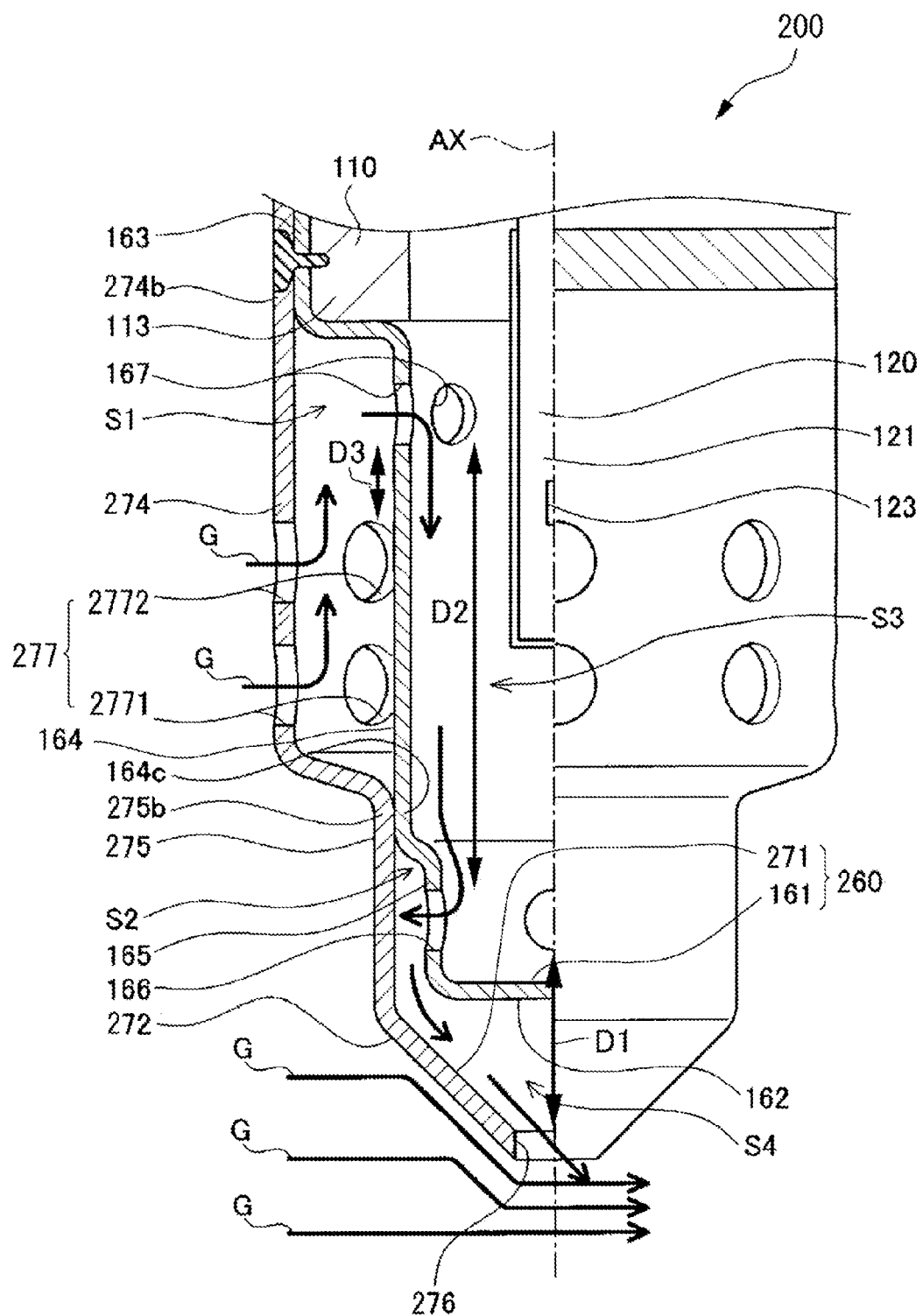
FIG. 5 is a half sectional view of a portion in the vicinity of a protector of a gas sensor of an embodiment according to a second mode of the present invention.

FIG. 5 is a half sectional view of a gas sensor 200 of an embodiment according to the second mode of the present invention, and shows a portion in the vicinity of a protector of the gas sensor 200. The gas sensor 200 has the same configuration as the gas sensor 100 except for a protector 260 (in particular, an outer protector 271). Therefore, description of components other than the protector 260 is omitted. In addition, elements in common between the protector 260 and the protector 160 are denoted by the same reference numerals, and repeated description thereof is omitted.

Similar to the case of the first mode, the outer protector 271 is fixed to a metallic shell 110 in a state in which the outer protector 271 accommodates an inner protector 161 therein. The outer protector 271 has a first outer wall 274; a second outer wall 275 located on the axially forward end side of the first outer wall 274, and a taper wall 272 (corresponding to the "outer bottom wall" of the invention) located on the axially forward end side of the second outer wall 275 (see FIG. 5).

The first outer wall 274 has a cylindrical tubular shape, and surrounds the circumference of a first inner wall 164 while forming a tubular first space S1 in cooperation with the first inner wall 164 of the inner protector 161. Further, the first outer wall 274 has first outer holes 277 which penetrate the first outer wall 274 and are located on the axially forward end side in relation to first inner holes 167 of the inner protector 161 (see FIG. 5). Notably, in the present embodiment, as shown in FIG. 5, eight first outer holes 2771 having the same shape (same dimension) are provided at equal intervals in the circumferential direction on the forward end side of the first outer wall 274. In addition, eight first outer holes 2772 having the same shape (same dimension) are provided at equal intervals in the circumferential direction on the rear end side in relation to the first outer holes 2771. Thus, the first outer holes 2771 and 2772 (which are collectively denoted by reference numeral 277) are arranged in two rows in the direction of the axis AX. Each of the first outer holes 2771 and 2772 has the same shape and dimension as each of the first outer holes 177, and the total number of the first outer holes 277 is 16. Therefore, the total opening area D of the first outer holes 277 is twice the total opening area D of the first outer holes 177 of the gas sensor 100.

The second outer wall 275 has a cylindrical tubular shape, and has an inner diameter smaller than the inner diameter of the first outer wall 274 and larger than the outer diameter of the first inner wall 164. Further, the second outer wall 275 surrounds the circumference of the second inner wall 165 while providing a tubular second space S2 in cooperation with the second inner wall 165. The second outer wall 275 extends to a point on the axially forward end side of an inner bottom wall 162 of the inner protector 161.

In particular, in the present embodiment, the second outer wall 275 is connected at its base end portion 275b to a forward end portion 164c of the first inner wall 164 in an airtight manner (in a state in which gas cannot flow through the connected portion). Specifically, the base end portion 275b of the second outer wall 275 and the forward end portion 164c of the first inner wall 164 are airtightly connected (fitted) together over the entire circumference around the axis AX by means of press-fitting the forward end portion 164c of the first inner wall 164 into the base end portion 275b of the second outer wall 275.

A taper wall 272 has the shape of a tapered tube (truncated conical tube) whose diameter decreases toward the axially forward end side. This taper wall 272 has a second outer hole 276, which is a forward end opening of the outer protector 271. In particular, in the present embodiment, the entirety of the taper wall 272 is disposed on the axially forward end side in relation to the inner bottom wall 162 of the inner protector 161.

A base end portion 274b of the first outer wall 274 of the outer protector 271 is disposed on the outer side of a base end portion 163 of the inner protector 161. Laser welding is performed along the entire outer circumference of the base end portion 274b of the outer protector 271 so as to fix (weld) the base end portion 274b of the outer protector 271, together with the base end portion 163 of the inner protector 161, to a forward end fixing portion 113 of a metallic shell 110.

In the gas sensor 200 of the present embodiment, exhaust gas (gas-to-be-detected) G within the exhaust pipe flows through the interior of the protector 260 (the inner protector 161 and the outer protector 271) along the following route.

Specifically, as shown in FIG. 5, the exhaust gas G having flowed through the exhaust pipe from the upstream side thereof (the left side in FIG. 5) toward the gas sensor 200 is introduced into the first space S1 within the protector 160 (the space between the first outer wall 274 and the first inner wall 164) through the first outer holes 2771 and 2772 of the outer protector 271.

The exhaust gas G then flows within the first space S1 toward the axially base end side (the upper side in FIG. 5), and is introduced into an internal space S3 of the inner protector 161 through first inner holes 167 of the inner protector 161 (inner gas introduction holes). Thereafter, the exhaust gas G flows within the internal space S3 toward the axially forward end side (the lower side in FIG. 5), is discharged to the outside of the inner protector 161 through second inner holes 166 of the inner protector 161 (inner gas discharge holes), and is introduced into the second space S2 (the space between the second outer wall 275 and the second inner wall 165). After being introduced into an in-taper space S4 surrounded by the taper wall 272 of the outer protector 271, the exhaust gas G is discharged to the outside of the protector 260 through the second outer hole 276 (outer gas discharge hole) of the outer protector 271.

In the gas sensor 200 of the present embodiment, the base end portion 275b of the second outer wall 275 of the outer protector 271 is connected to (fitted onto) the forward end portion 164c of the first inner wall 164 of the inner protector 161 over the entire circumference around the axis in an airtight manner (in a state in which gas cannot flow through the connected portion).

Therefore, the exhaust gas G introduced into the first space S1 from the outside through the first outer holes 2771 and 2772 does not flow from the first space S1 directly to the second space S2. Instead, the exhaust gas G flows within the first space S1 toward the axially base end side without fail, and is introduced into the internal space S3 of the inner protector 161 (space which accommodates the detection portion 120 of the detection element 120) through the first inner holes 167 (see FIG. 5). Thus, the exhaust gas G introduced into the internal space S3 of the inner protector 161 through the first inner holes 167 can be smoothly discharged to the outside of the inner protector 161 through the second inner holes 166.

In the gas sensor 200 of the present embodiment, the total opening area A of the second outer hole 276, the total opening area B of the second inner holes 166, the total opening area C of the first inner holes 167, and the total opening area D of the first outer holes 2771 and 2772 satisfy a relation of A≤B<C<D. That is, of the total opening areas of the second outer hole 276, the second inner holes 166, the first inner holes 167, and the first outer holes 2771 and 2772, the total opening area A of the second outer hole 276 is made smallest. Accordingly, in the gas sensor 200 of the embodiment, the amount of gas discharged to the outside of the protector 260 (discharge performance) is adjusted by the second outer hole 276 without being affected by the gas discharge performances of the second inner holes 166, the first outer holes 2771 and 2772, and the first inner holes 167.

In addition, of the total opening areas of the first outer holes 2771 and 2772, the first inner holes 167, the second inner holes 166, and the second outer hole 276, the total opening area D of the first outer holes 2771 and 2772 is made largest. Therefore, the exhaust gas G is easily introduced from the outside into the protector 260 through the first outer holes 2771 and 2772. Thus, the responsiveness of the gas sensor can be enhanced. Since the total opening area C of the first inner holes 167 is made largest next to the total opening area D of the first outer holes 2771 and 2772, the exhaust gas G is easily introduced into the internal space S3 of the inner protector 161 through the first inner holes 167, whereby the responsiveness of the gas sensor can be enhanced.

Also, D3 is smaller than D1 and smaller than D2, wherein D1 represents the shortest distance (in the direction of the axis AX) between the second outer hole 276 and the second inner holes 166, D2 represents the shortest distance (in the direction of the axis AX) between the second inner holes 166 and the first inner holes 167, and D3 represents the shortest distance (in the direction of the axis AX) between the first inner holes 167 and the first outer holes 2772.

Thus, the shortest distance D3 is smaller than D1 and smaller than D2. When the distance D3 is made shortest, the gas is easily introduced from the outside into the protector 260, since the gas introduced into the protector 260 firstly passes between the first outer holes 2771 and 2772 and the first inner holes 167. Therefore, the responsiveness of the gas sensor 200 can be enhanced.

As used herein, the term "axially shortest distance" between holes refers to the shortest linear distance between the holes in the direction of the axis AX. For example, the shortest distance D3 between the first inner hole 167 and the first outer holes 2771 and 2772 corresponds to the shortest linear distance (in the direction of the axis AX) between the base-end-side peripheral edge of the first outer hole 2772 (which is nearer to the first inner hole 167 than the first outer hole 2771) and the forward-end-side peripheral edge of the first inner hole 167 as viewed in a radial direction perpendicular to the axial direction (see FIG. 5). In other words, as shown in FIG. 5, the "axially shortest distance" corresponds to the shortest distance (in the direction of the axis AX) of corresponding projection holes of (the first outer holes 2771 and 2772, the first inner hole 167, the second inner hole 166, and the second outer hole 276), the projection holes being provided through projection of the protector on a paper sheet.

When the shortest distance D3 is made smaller than D1 and smaller than D2; i.e., the first outer holes 2772 approach the first inner holes 167 in the direction of the axis AX, the responsiveness of the gas sensor 200 can be enhanced. However, when the first outer holes 2772 approach the first inner holes 167, the first outer holes 2772 and the first inner holes 167 axially overlap one another. In this case, when water enters from the outside into the first outer holes 2772, the water easily flows directly into the first inner holes 167 (into the inner protector 161). Thus, when a plurality of first outer holes 277 are provided in the axial direction (i.e., the first outer holes 2771 and 2772 are provided in the axial direction), water entering through the first outer holes 277 is easily discharged to the outside, and is prevented from flowing into the inner protector 161, whereby the detection element 120 accommodated within the inner protector 161 can be effectively protected from adhesion of water.

Although the present invention has been described in reference to the above embodiments thereof, the present invention is not limited thereto. That is, the present invention may be implemented with appropriate modifications without departing from the scope of the invention.

For example, in the embodiments, the gas sensor 100 or 200 is a full-range air/fuel ratio sensor. However, the present invention can be applied to oxygen sensors, NOx sensors, HC sensors, etc.

Also, in the present embodiment, the base end portion 175b of the second outer wall 175 and the forward end portion 164c of the first inner wall 164 are airtightly connected by press-insertion (fitting) of the forward end portion 164c of the first inner wall 164 into the base end portion 175b of the second outer wall 175. However, the manner of airtightly connecting the base end portion of the second outer wall and the forward end portion of the first inner wall is not limited to fitting. For example, the base end portion of the second outer wall and the forward end portion of the first inner wall may be airtightly connected together by crimping or welding (welding over the entire circumference).

In the present embodiment, the base end portion 175b of the second outer wall 175 and the forward end portion 164c of the first inner wall 164 are airtightly connected. However, the present invention is not limited thereto. The base end portion 175b and the forward end portion 164c may be separated from each other while overlapping with each other in a radial direction.

In the first mode, the number of the first outer holes 177 is 8, the number of the first inner holes 167 is 8, and the number of the second inner holes 166 is 4, whereas in the second mode, the number of the first outer holes 277 is 16, the number of the first inner holes 167 is 8, and the number of the second inner holes 166 is 4. However, the numbers of the first outer holes, the first inner holes, and the second inner holes may be appropriately determined so as to satisfy the above-described relation among their total opening areas. Therefore, the embodiments may be modified such that the first outer holes, the first inner holes, and the second inner holes are rendered the same in number, and the opening area per hole of the first outer holes, that of the first inner holes, and that of the second inner holes are properly set so as to satisfy the above-described relation among their total opening areas.

In the second mode, the first outer holes 2771 or 2772 are provided at equal intervals in the circumferential direction, and the shape and number of the first outer holes 2771 are the same as those of the first outer holes 2772. However, when a plurality of first outer holes 2771 and 2772 are provided in the direction of the axis AX, the first outer holes are not necessarily aligned parallel to the direction of the axis AX, or the number of the first outer holes provided at a position (in the direction of the axis AX) may differ from that of the first outer holes provided at another position (in the direction of the axis AX). For example, the number of the first outer holes 2771 may be 4, and the number of the first outer holes 2772 may be 6. Alternatively, the first outer holes 2771 and 2772 may have different sizes.

Examples

A gas sensor (oxygen sensor) 100 shown in FIGS. 1 to 5 was produced. Table 1 shows the size and number of holes (circular holes) provided on an inner protector 161 and an outer protector 171 of the gas sensor 100. In the outer protector 171, the outer diameter of a first outer wall 174 was adjusted to 9.3 mm, and the outer diameter of a second outer wall 175 was adjusted to 13.8 mm.

TABLE 1

|  | Diameter (mm) | Number | Total opening area (mm$^2$) |
| --- | --- | --- | --- |
| Second outer hole | 2.0 | 1 | (A=) 3.14 |
| Second inner hole | 1.5 | 4 | (B=) 7.07 |
| First inner hole | 1.5 | 8 | (C=) 14.14 |
| First outer hole | 2.0 | 8 | (D=) 25.13 |

Subsequently, the gas sensor 100 was attached to an exhaust pipe of an engine, and a temperature sensor was also provided in the vicinity of the gas sensor 100 so as to measure the temperature of exhaust gas. For determining the responsiveness of the gas sensor 100, the engine was operated under the following condition A or B:

Condition A: engine rotation speed: 3,000 rpm, intake manifold negative pressure: −46 kPa, exhaust gas temperature in the vicinity of the gas sensor 100: 540° C.; or Condition B: engine rotation speed: 5,000 rpm, intake manifold negative pressure: −62 kPa, exhaust gas temperature in the vicinity of the gas sensor 100: 710° C.

The responsiveness of the gas sensor 100 was evaluated on the basis of sensor signal amplitude at the time of imbalance. The larger the sensor signal amplitude, the higher the responsiveness.

<Experiment 1>

Figure 6:
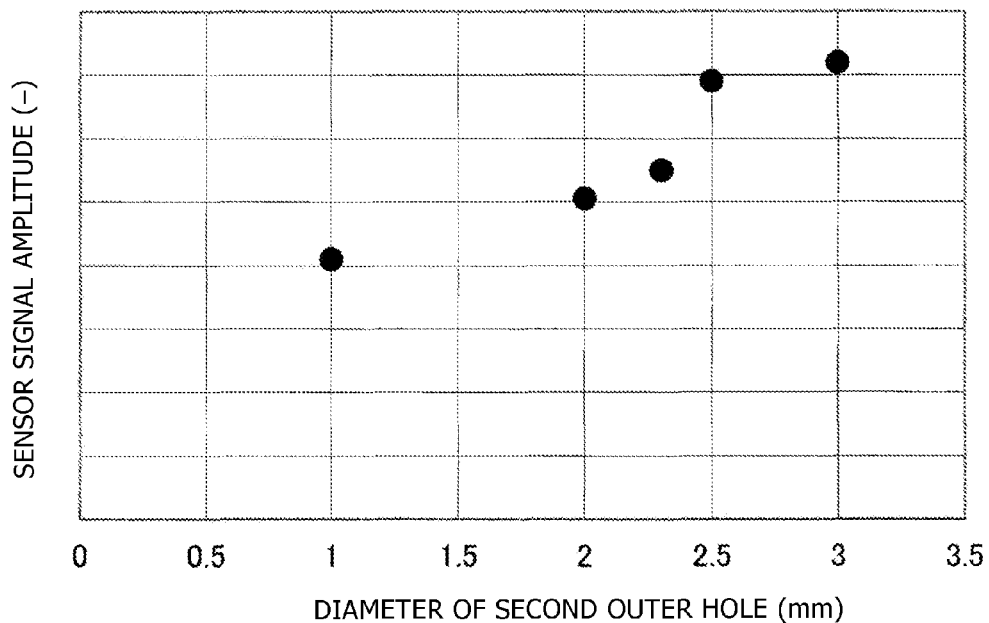
FIG. 6 is a graph showing the relationship between the diameter of a second outer hole and the responsiveness of a gas sensor (sensor signal amplitude).

Gas sensors 100 were produced having second outer holes 176 with varied diameters (shown in Table 2). Each of the gas sensors 100 was attached to an exhaust pipe of an engine, and the responsiveness of the gas sensor 100 was determined during operation of the engine under Condition B. The results are shown in FIG. 6. In experiment 1, the shortest distance D1 was adjusted to 4.0 mm, the shortest distance D2 was adjusted to 13.1 mm, and the shortest distance D3 was adjusted to 5.4 mm.

TABLE 2

|  | Comp. Ex. 1 | Comp. Ex. 2 | Comp. Ex. 3 | Ex. 1 | Ex. 2 |
| --- | --- | --- | --- | --- | --- |
| Diameter of second outer hole (mm) | 1.0 | 2.0 | 2.3 | 2.5 | 3.0 |
| Total opening area A (mm$^2$) | 0.79 | 3.14 | 4.15 | 4.91 | 7.07 |
| A/B | 0.11 | 0.44 | 0.59 | 0.69 | 1.00 |

As shown in FIG. 6, in the case of Example 1 or 2 wherein (0.6×B)≤A, the responsiveness of the gas sensor was considerably improved, as compared with Comparative Examples 1 to 3 wherein (0.6×B)>A.

<Experiment 2>

Figure 7:
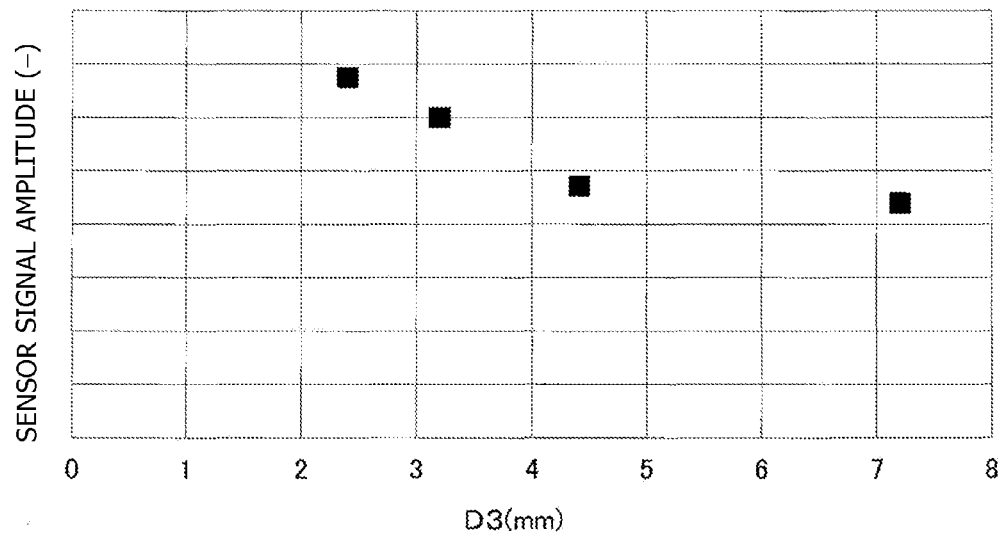
FIG. 7 is a graph showing the relationship between shortest distance D3 and the responsiveness of a gas sensor (sensor signal amplitude).

Gas sensors 100 were produced having holes 166, 167, 176, and 177 provided at different positions, in which the shortest distances D1 to D3 were changed as shown in Table 3. Each of the gas sensors 100 was attached to an exhaust pipe of an engine, and the responsiveness of the gas sensor 100 was determined during operation of the engine under condition A. The results are shown in FIG. 7. The size and number of the holes 166, 167, 176, or 177 are shown in Table 1.

TABLE 3

|  | Comp. Ex. 10 | Comp. Ex. 11 | Ex. 11 | Ex. 12 |
| --- | --- | --- | --- | --- |
| Shortest distance D1 (mm) | 4 | 4 | 4 | 4 |
| Shortest distance D2 (mm) | 13.1 | 13.1 | 13.1 | 13.1 |
| Shortest distance D3 (mm) | 5.4 | 4.4 | 3.2 | 2.4 |
| Shortest distance | Distance between A and B | Distance between A and B | Distance between C and D | Distance between C and D |

As shown in FIG. 7, in the case of Example 11 or 12 wherein the shortest distance D3 was smaller than D1 and smaller than D2, gas quickly reached the detection element 120 within the protector 160 (i.e., the responsiveness of the gas sensor was considerably improved), as compared with Comparative Examples 10 and 11 wherein the shortest distance D1 was smaller than D2 and smaller than D3.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2013-215210, filed Oct. 16, 2013, incorporated herein by reference in its entirety.

What is claimed is:

1. A gas sensor comprising:
a detection element extending in an axial direction and having a detection portion which is provided on a forward end side thereof and adapted to detect a particular gas component contained in a gas-to-be-detected;
a housing which surrounds a circumference of the detection element such that the detection portion projects from a forward end of the housing; and
a protector which is fixed to the housing and which surrounds the circumference of the detection portion, the protector including an inner protector which accommodates the detection portion in an internal space of the inner protector, and an outer protector which accommodates the inner protector, wherein
the inner protector includes
a tubular first inner wall having a first inner hole extending therethrough,
a tubular second inner wall which is located on an axially forward end side of the first inner wall and which has a diameter smaller than that of the first inner wall, the second inner wall having a second inner hole extending therethrough, and an inner bottom wall which closes a forward end of the second inner wall;

the outer protector includes a tubular first outer wall which surrounds the circumference of the first inner wall to define a tubular first space between the first outer wall and the first inner wall, the first outer wall having a first outer hole extending therethrough at a position on the axially forward end side in relation to the first inner hole, a tubular second outer wall which is located on the axially forward end side of the first outer wall, which has a diameter smaller than that of the first outer wall and larger than that of the first inner wall, and which surrounds the circumference of the second inner wall to define a tubular second space between the second outer wall and the second inner wall, the second outer wall having a base end portion which radially overlaps a forward end portion of the first inner wall, and extending toward the axially forward end side in relation to the inner bottom wall, and an outer bottom wall located on the axially forward end side of the second outer wall and having a second outer hole; and relations of $A \leq B < C < D$ and $(0.6 \times B) \leq A$ are satisfied, wherein A represents the total opening area of the second outer hole, B represents the total opening area of the second inner hole, C represents the total opening area of the first inner hole, and D represents the total opening area of the first outer hole.

2. A gas sensor comprising:

a detection element extending in an axial direction and having a detection portion which is provided on a forward end side thereof and adapted to detect a particular gas component contained in a gas-to-be-detected;

a housing which surrounds a circumference of the detection element such that the detection portion projects from a forward end of the housing; and a protector which is fixed to the housing and which surrounds the circumference of the detection portion, the protector including an inner protector which accommodates the detection portion in an internal space of the inner protector, and an outer protector which accommodates the inner protector, wherein the inner protector includes a tubular first inner wall having a first inner hole extending therethrough, a tubular second inner wall which is located on an axially forward end side of the first inner wall and which has a diameter smaller than that of the first inner wall, the second inner wall having a second inner hole extending therethrough, and an inner bottom wall which closes a forward end of the second inner wall;

the outer protector includes a tubular first outer wall which surrounds the circumference of the first inner wall to define a tubular first space between the first outer wall and the first inner wall, the first outer wall having a first outer hole extending therethrough at a position on the axially forward end side in relation to the first inner hole, a tubular second outer wall which is located on the axially forward end side of the first outer wall, which has a diameter smaller than that of the first outer wall and larger than that of the first inner wall, and which surrounds the circumference of the second inner wall to define a tubular second space between the second outer wall and the second inner wall, the second outer wall having a base end portion which radially overlaps a forward end portion of the first inner wall, and extending toward the axially forward end side in relation to the inner bottom wall, and an outer bottom wall located on the axially forward end side of the second outer wall and having a second outer hole;

a relation of $A \leq B < C < D$ is satisfied, wherein A represents the total opening area of the second outer hole, B represents the total opening area of the second inner hole, C represents the total opening area of the first inner hole, and D represents the total opening area of the first outer hole; and D3 is smaller than D1 and smaller than D2, wherein D1 represents the axially shortest distance between the second outer hole and the second inner hole, D2 represents the axially shortest distance between the second inner hole and the first inner hole, and D3 represents the axially shortest distance between the first inner hole and the first outer hole.

3. The gas sensor as claimed in claim 1, wherein the base end portion of the second outer wall is connected airtightly to the forward end portion of the first inner wall.

4. The gas sensor as claimed in claim 2, wherein the base end portion of the second outer wall is connected airtightly to the forward end portion of the first inner wall.

5. The gas sensor as claimed in claim 1, wherein a plurality of first outer holes are provided in the axial direction.

6. The gas sensor as claimed in claim 2, wherein a plurality of first outer holes are provided in the axial direction.

7. The gas sensor as claimed in claim 1, wherein the outer bottom wall is tapered toward the axially forward end side.

8. The gas sensor as claimed in claim 2, wherein the outer bottom wall is tapered toward the axially forward end side.

9. The gas sensor as claimed in claim 1, wherein the detection element has a gas introduction portion for introducing the gas-to-be-detected into the detection portion; and the first inner hole is located on the axially base end side in relation to the gas introduction portion.

10. The gas sensor as claimed in claim 2, wherein the detection element has a gas introduction portion for introducing the gas-to-be-detected into the detection portion; and the first inner hole is located on the axially base end side in relation to the gas introduction portion.

* * * * *